United States Patent [19]

Lecacheux et al.

[11] Patent Number: 4,478,071
[45] Date of Patent: Oct. 23, 1984

[54] VISCOSIMETER OPERATING CONTINUOUSLY ESPECIALLY AT HIGH TEMPERATURE

[75] Inventors: Didier Lecacheux, Chilly Mazarin; James Lesec, Saint-Leu-La Foret; Roland Prechner, Pau, all of France

[73] Assignee: Societe Nationale Elf Aquitaine, Courbevoie, France

[21] Appl. No.: 451,750

[22] Filed: Dec. 21, 1982

[30] Foreign Application Priority Data

Dec. 29, 1981 [FR] France ................ 8124382

[51] Int. Cl.³ .................................... G01N 11/04
[52] U.S. Cl. ........................................... 073/55
[58] Field of Search ............................ 73/54, 55, 56

[56] References Cited

U.S. PATENT DOCUMENTS

| | | | |
|---|---|---|---|
| 1,534,091 | 4/1925 | Smoot | 73/55 X |
| 2,459,483 | 1/1949 | Zimmer et al. | 73/55 |
| 3,024,643 | 3/1962 | Jones, Jr. | 73/55 |
| 3,115,768 | 12/1963 | Rhodes et al. | 73/55 |
| 3,548,638 | 12/1970 | Uchida et al. | 73/55 |
| 3,720,097 | 3/1973 | Kron | 73/55 |
| 3,962,907 | 6/1976 | Peyrouset et al. | 73/55 |
| 4,165,632 | 8/1979 | Weber et al. | 73/55 |

Primary Examiner—S. Clement Swisher
Assistant Examiner—Hezron Williams
Attorney, Agent, or Firm—Burgess, Ryan & Wayne

[57] ABSTRACT

The present invention concerns a viscosimeter adapted to operate continuously, comprising a measuring capillary in which the liquid phase whose viscosity is measured undergoes a loss of pressure. It is characterized in that the measuring capillary (17) consists of a tube of several meters length, wound around itself according to a helix having a diameter of at least 10 cm, the internal diameter of the tube being substantially comprised between 0.20 and 0.30 mm, and in that a sensor for measuring the loss of pressure consists of two identical pressure sensors (22,23) positioned at the entry and at the exit of the capillary (17) for differentially measuring the loss of pressure in this capillary.

9 Claims, 2 Drawing Figures

VISCOSIMETER OPERATING CONTINUOUSLY ESPECIALLY AT HIGH TEMPERATURE

BACKGROUND OF THE INVENTION

The present invention concerns a viscosimeter, more particularly, a viscosimeter adapted to be associated with a gel permeation chromatography device (GPC) operating in liquid phase, said viscosimeter being destined for continuous operation, especially for the characterization of polymers.

It is therefore possible to characterize the distribution curves and the mean molecular weights of the synthetic or natural polymers, and also the branching rate of the macromolecules, and, more generally, all the structural parameters of the molecules involved.

However, one object of the invention is the production of such a viscosimeter capable of being used at high temperature and thus suitable for the characterization of the polymers, especially the polyolefins.

DESCRIPTION OF THE PRIOR ART

The principle of gel permeation chromatography is simple. It consists in passing a solution of macromolecules through a porous support. The longest chain products can only penetrate in pores having a large enough diameter whereas the oligomers pass through a part of the porous volume and, thus subsequently exit from the column. In order to take into account this phenomenon of steric exclusion, BENOIT proposed the use of parameter $\{\eta\}.M$, which is proportional to the hydrodynamic volume of the macromolecule in solution. ($\{\eta\}$ is the intrinsic viscosity and M the molecular weight). The validity of the universal calibration principle was checked not only for the linear polymers of all kinds but also for the branched polymers.

The GPC thus allows the separation of the constituents of samples according to their hydrodynamic volume. This is a relative method: it necessitates a previous calibration of the set of columns in accordance with the equation $\log (\{\eta\}.M)=f(Ve)$ where Ve is the elution volume. The detection of the polymer in the eluate is carried out by means of a concentration detector (RI,UV) that supplies a distribution curve as a function of the hydrodynamic volume. But, in order to reach the various mean molecular weights and possibly the branching index of the analysed sample, it is necessary to measure the intrinsic viscosity of $\{\eta\}$ in function of the elution volume.

The viscosimeter according to the present invention allows such a measurement to be taken.

With respect to the GPC on standard supports (packing of about $50\mu$), the possibility of a viscosimetric detection of the effluent has been known since 1968. Its principle is the following: at the exit of the columns, a counting siphon discharges at regular intervals a constant volume of the mobile phase into a suitably modified standard viscosimeter. The automatic measurement of fall time (t) allows determination of the intrinsic viscosity $\{\eta\}_i$ of each fraction i. Indeed, the usual quantities always being very small in GPC (C<0.05%), it is possible to write $$\{\eta\}_i = \frac{1}{C_i} \ln \frac{t_i}{t_o}$$

in which the index 0 represents the pure solvent.

The micro-packings (about $10\mu$) that appeared in 1974 superseded the previous system. Indeed, whereas the fractioning had taken place on 10–50 milliliters samples, the useful volume in HPLC (high pressure liquid chromatography) can be reduced to a few milliliters. This is the reason why the rapid GPC can only be coupled to a viscosimeteric detector of the type described by OUANO: a pressure sensor for continuous measurement of the loss of pressure in a pressure sensor having a small internal diameter. This is an application of POISEUILLE'S law:

$$P = k.\eta.d$$

in which
P is the loss of pressure,
$\eta$ is the absolute viscosity of the mobile phase,
d is the output,
k is a constant characteristic of the apparatus.

The intrinsic viscosity $\{\eta\}_i$ is obtained as a function of time according to $$\{\eta\}_i = \frac{1}{C_i} \ln \frac{P_i}{P_o}$$

the out-put being strictly constant throughout the analysis.

The division of the chromatogram into a certain number of points only depends here upon possibilities of calculation; the volume increments can be chosen in such a way as to represent any product by about a hundred fractions.

From simultaneous values $\{\eta\}_i$, is subtracted the molecular weight M, present in the fraction i due to the principle of universal calibration:

$$(\{\eta\}.M)_i = \{\eta\}_i.M_i.$$

The results concerning the product as a whole are thus easily calculated according to the standard averages:

$$\overline{Mn} = \frac{\sum\limits_i C_i}{\sum\limits_i \frac{C_i}{M_i}} \quad \overline{Mw} = \frac{\sum\limits_i C_i M_i}{\sum\limits_i C_i}, \quad \{\eta\} = \frac{\sum\limits_i \{\eta\}_i C_i}{\sum\limits_i C_i}$$

In the case of branched polymers, it is easy to deduce from experimental viscosity relations, the variation of the frequency of the branches with the molecular weight.

The viscosimeter according to the present invention is particularly adapted for:
the study of organosoluble polymers at ambient temperature;
the GPC in water;
the characterization of polyolefins at high temperature, etc.

Furthermore, a viscosimeter according to the invention can constitute an extremely sensitive flow meter and thus supply operating means, for the control of a chromatographic system as a whole.

SUMMARY OF THE INVENTION

A viscosimeter according to the present invention, adapted for continuous operation, comprising a measuring capillary in which the liquid phase whose viscosity is measured undergoes a loss of pressure, this viscosimeter comprising means for measuring said loss of pressure being characterized in that the measuring capillary consists of a tube having a length of several meters, wound about itself according to a helix, having a diameter of at least 10 cm, the internal diameter of said tube being substantially comprised between 0.2 and 0.30 mm, and in that the means of measuring said loss of pressure consist of two similar pressure sensors, positioned at the entry and exit of said capillary in order to allow a differential measurement of the loss of pressure in the capillary.

According to one embodiment of the invention, the measuring capillary is arranged in a thermostat-controlled bath. When operating occurs at high temperatures, for example 150° C., in the case of polyolefins, the assembly of the device, excepting the solvent, at entry 13 and exit 32, is placed in an oven maintained at this high temperature of 150° C.

According to another embodiment of the invention, the measuring capillary is arranged in a thermostat-controlled bath; preferably the assembly excepting 13 and 32, is placed in a thermostat-controlled oven, for example at 150° C. or another high temperature. The bath 25 is preferably reserved for temperatures close to ambient, in any event <80°-100° C.

According to another embodiment of the invention the diameter of the capillary helix is at least 10 cm, and preferably 16-17 cm, its internal diameter is 0.27 mm and its total length about 3 m.

According to a further embodiment of the invention, the pressure sensors are connected to two terminals 20 and 21 upstream and downstream from the measuring capillary by two T-shaped connectors or T-connectors into which lead respectively the delivery and dispatch conduits of the measured liquid phase. The pressure sensors are associated to a device for processing the signals that they deliver, comprising an amplifier.

The present invention also concerns an installation for continuous measurement of the viscosity of the liquid phase exiting from a chromatography volume in liquid phase, said column being equipped with a pump and a nozzle, the installation comprising a viscosimeter such as defined herein-above and being characterized in that the exit of the column is connected to the entry of the measuring capillary, the indications of the pressure sensors being transmitted to an information treatment chain integrated to the installation.

According to another form of operation of the above-mentioned installation, the exit of the measuring capillary is connected to a refractometer for measuring the refraction index of the liquid phase having passed through the capillary, the refractometer being integrated to the installation.

As shown here-under, the two pressure sensors allow precise measurement of the loss of pressure in the measuring capillary alone, independently of the flow characteristics of the circuit downstream from this capillary. Thus is obtained a precise determination of the viscosity, due, furthermore, to the fact that the diameter of the winding helix of the capillary tube is very large relative to the internal diameter of the capillary tube. The values of the intrinsic viscosity measurements carried out continuously with the viscosimeter according to the invention correspond well with the static measurements of this viscosity.

BRIEF DESCRIPTION OF THE DRAWING

The characteristics and advantages of the present invention, however, will become more apparent from reading through the following description, given simply by way of non-limitative example, with reference to the annexed drawings in which.

DETAILED DESCRIPTION OF THE DRAWINGS

Figure 1:
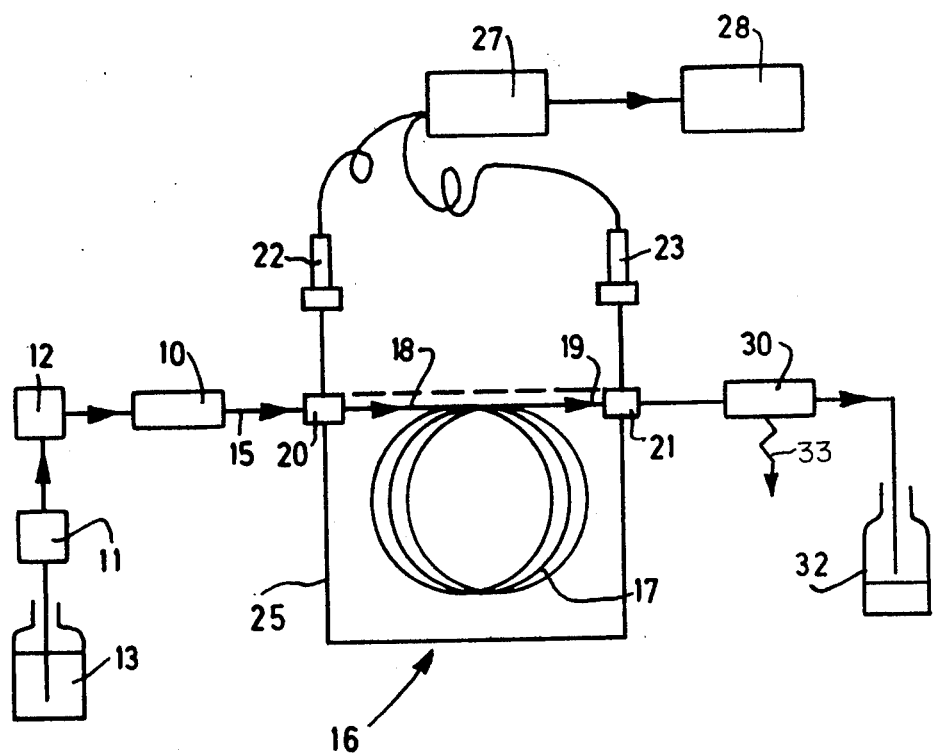
FIGS. 1 and 2 represents diagrammatically an installation for the continuous measurement of the viscosity of the liquid phase which exits from a chromatography column on gel in the liquid phase, comprising a viscosimeter according to the invention.

In the embodiment described and represented in the single diagram annexed, the viscosimeter according to the invention is associated to a chromatography installation on gel in a liquid phase, which is itself associated to a refractometer, allowing, by measurement of the index variations of the liquid phase, to follow its polymer concentration.

This installation normally comprises a set of chromatography columns 10, provided with a pump 11 and a nozzle 12, the pump being fed by solvent 13, for example THF.

The exit 15 of columns 10 is connected to the viscosimeter itself, indicated by the general reference 16. The viscosimeter comprises a measuring capillary 17 constituted by a capillary tube of several meters, for example, 3 meters, presenting a reduced internal diameter, comprised subsantially between 0.20 and 0.30 mm wound about itself in order to substantially form a helix having a large diameter, of at least 10 cm, for example 16 cm. The internal volume of the capillary is extremely reduced to several hundred microliters.

At entry 18 and exit 19 of the measuring capillary 17, are connected by means of two T-shaped connectors or T-connectors 20 and 21 respectively, two identical pressure sensors 22 and 23 respectively.

The capillary tube 17 is, for example, emerged in a thermostat controlled-bath 25, the temperature of which is maintained at a temperature close to ambient; such a thermostat-controlled bath can, however, be used for operating temperatures reaching 100° C.

Figure 2:
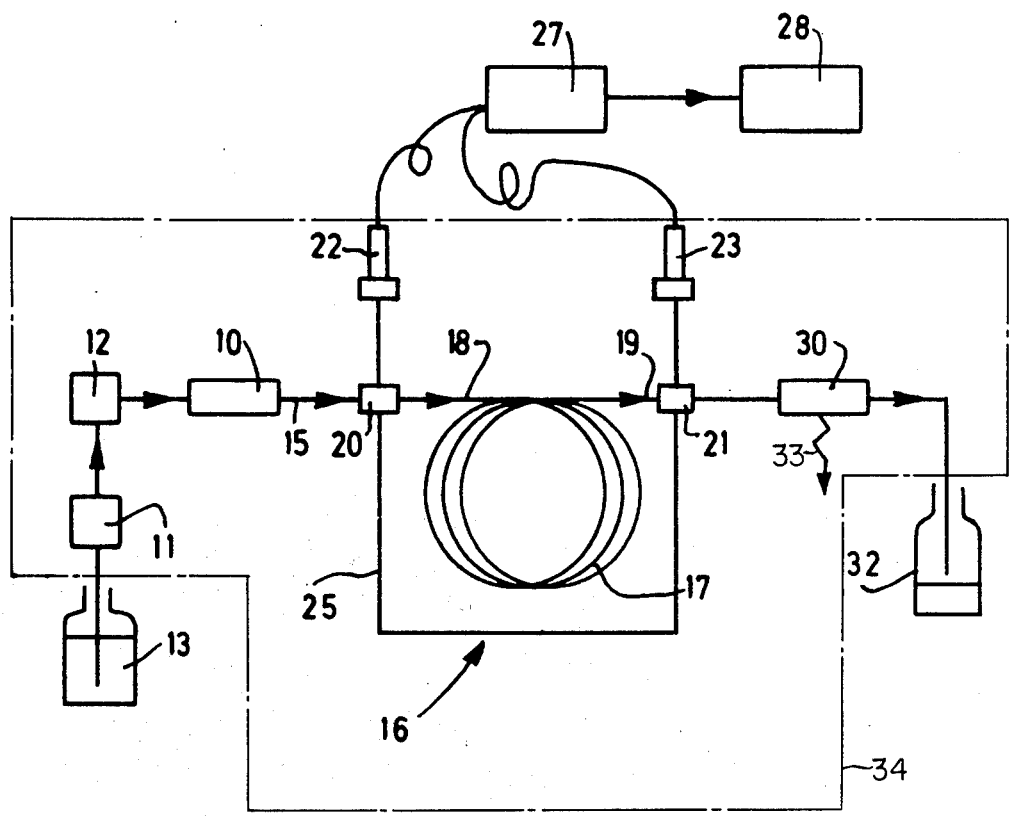

In the case where the device according to the invention is applied to measuring polyolefins, ie. must operate at high temperatures in the range of 150° C., the device assembly, with the exception, however, of solvent 13 at the entry, and 32 at the exit, is placed in a thermostat-controlled oven 34 maintained at said high temperature. The oven 34 is noted by the dashed line shown in FIG. 2.

Pressure sensors 22 and 23 are connected to an amplifier 27 and their amplified indications are exploited in a processing chain diagrammatized in 28. Thus it is possible to measure with precision the loss of charge in the capillary and, by applying POISEUILLE'S formula, to determine as shown hereabove the intrinsic viscosity $\{\eta\}$.

The exit 19 of the capillary tube is connected to a refractometer 30 and the used solvent that exits from the refractometer after being measured is recovered in 32.

The refractometer 30 supplies a signal 33, function of the concentration, that completes the indications provided by the viscosimeter.

It will be noted that due to the presence of the two pressure sensors 22 and 23, only the loss of charge effectively intervening in the measuring capillary is measured, by eliminating totally the loss of charge inevitably introduced by the refractometer or any other component of the downstream circuit.

The inventors have shown, furthermore, that in a capillary, the winding of said capillary was at the origin of a singular loss of pressure P' which adds to the POISEUILLE term $P_p$; thus the total loss of pressure $P = P' + P_p$.

The P' term in fact renders incorrect the viscosity measurements of a continuously operating viscosimeter. This is due to the effect of the centrifugal force and becomes negligible for winding turns having a diameter larger than 10 cm, which was adopted for the viscosimeter according to the invention.

In the device of the present invention a pressure change according to POISEUILLE's law is obtained because of the winding configuration upstream of the second sensor 23. The intrinsic viscosity measurements thus correspond excellently with the results of static methods.

Of course, the present invention is in no way limited to the embodiments described annd represented herein; it can be adapted to numerous variants available to the man skilled in the art without departing from the spirit of the invention.

We claim:

1. Viscosimeter designed for continuous operation, comprising a measuring capillary in which the liquid phase whose viscosity is measured, undergoes a loss of pressure, the measuring capillary consisting of a tube having a length of several meters, wound around itself in the form of a helix having a diameter of at least 10 cm, the internal diameter of the said tube being substantially between 0.20 and 0.30 mm, and means of measuring the said loss of pressure said measuring means comprising two pressure sensors positioned at the entry and at the exit of the said capillary, for differential measurement of the loss of pressure in the capillary.

2. A viscosimeter according to claim 1, wherein the measuring capillary is arranged in a thermostatically-controlled bath.

3. A viscosimeter according to claim 1, wherein said viscosimeter is placed inside an oven maintained at high temperature.

4. A viscosimeter according to claim 3, wherein the temperature is in the range of 150° C., for measuring polyolefins.

5. A viscosimeter according to claim 1, 2, 3 or 4, wherein the diameter of the helix of the capillary is at least 10 cm, its internal diameter is 0.27 mm and its total length about 3 m.

6. A viscosimeter according to claim 1, 2, 3 or 4, wherein the diameter of the helix of the capillary is greater than 16 cm.

7. A viscosimeter according to claim 1, 2, 3 or 4, wherein the pressure sensors, are connected to two terminals upstream and downstream from the measuring capillary, by two T-connectors into which lead respectively the delivery and discharge conduits of the measured liquid phase.

8. A viscosimeter according to claim 1, 2, 3 or 4, wherein the pressure sensors are associated with a device for processing signals that they deliver, comprising an amplifier.

9. An installation for continuous measurement of the viscosity of a liquid phase exiting from a liquid chromatography column, in liquid phase, the column being provided with a pump and a nozzle, the installation comprising a viscosimeter according to claim 1, 2, 3 or 4, wherein the exit of the column is connected to the entry of the measuring capillary, the indications of the pressure, sensors being transmitted to an information processing chain integrated to the installation.

* * * * *